United States Patent
Seow et al.

(10) Patent No.: US 11,045,265 B2
(45) Date of Patent: Jun. 29, 2021

(54) ROBOTIC SURGICAL ASSEMBLIES AND INSTRUMENT DRIVE UNITS THEREOF

(71) Applicant: Covidien LP, Mansfield, MA (US)

(72) Inventors: Chi Min Seow, New Haven, CT (US); Mark MacLeod, Southbury, CT (US); Michael Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 220 days.

(21) Appl. No.: 16/304,425

(22) PCT Filed: May 24, 2017

(86) PCT No.: PCT/US2017/034206
§ 371 (c)(1),
(2) Date: Nov. 26, 2018

(87) PCT Pub. No.: WO2017/205481
PCT Pub. Date: Nov. 30, 2017

(65) Prior Publication Data
US 2019/0142535 A1    May 16, 2019

Related U.S. Application Data

(60) Provisional application No. 62/341,949, filed on May 26, 2016.

(51) Int. Cl.
*A61B 34/30* (2016.01)
*A61B 34/00* (2016.01)
(Continued)

(52) U.S. Cl.
CPC .............. *A61B 34/30* (2016.02); *A61B 34/00* (2016.02); *B25J 9/0009* (2013.01); *A61B 2017/00398* (2013.01); *A61B 2017/00477* (2013.01)

(58) Field of Classification Search
None
See application file for complete search history.

(56) References Cited

U.S. PATENT DOCUMENTS 2,602,308 A   7/1952   Bonnet
3,583,139 A   6/1971   Purrer
(Continued)

FOREIGN PATENT DOCUMENTS

CN      102014759 A      4/2011
DE      202008009571 U1  10/2008
(Continued)

OTHER PUBLICATIONS

European Search Report dated Dec. 20, 2019, corresponding to European Application No. 17803493.0; 12 pages.
(Continued)

*Primary Examiner* — Kennedy Schaetzle

(57) ABSTRACT

An instrument drive unit for use with a surgical robotic arm includes a body, a first gear, and a driven coupler. The body has a proximal end and a distal end configured to be coupled to a surgical instrument. The first gear is non-rotatably coupled to the proximal end of the body. The driven coupler is disposed at the proximal end of the body and laterally offset from the first gear. The driven coupler is operably coupled to the first gear such that rotation of the driven coupler rotates the first gear to effect rotation of the body about a longitudinal axis defined by the body.

14 Claims, 4 Drawing Sheets

(51) Int. Cl.
   *B25J 9/00* (2006.01)
   *A61B 17/00* (2006.01)

(56) References Cited

U.S. PATENT DOCUMENTS

| | | | |
|---|---|---|---|
| 4,897,014 | A | 1/1990 | Tietze |
| 5,748,767 | A | 5/1998 | Raab |
| 5,762,458 | A | 6/1998 | Wang et al. |
| 5,921,992 | A | 7/1999 | Costales et al. |
| 6,016,448 | A | 1/2000 | Busacker et al. |
| 6,063,095 | A | 5/2000 | Wang et al. |
| 6,076,525 | A | 6/2000 | Hoffman |
| 6,306,126 | B1 | 10/2001 | Moctezuma |
| 6,331,181 | B1 | 12/2001 | Tierney et al. |
| 6,416,415 | B1 | 7/2002 | Yu |
| 6,788,018 | B1 | 9/2004 | Blumenkranz |
| 6,824,471 | B2 | 11/2004 | Kamenov |
| 6,994,708 | B2 | 2/2006 | Manzo |
| 6,996,487 | B2 | 2/2006 | Jutras et al. |
| 7,035,716 | B2 | 4/2006 | Harris et al. |
| 7,118,564 | B2 | 10/2006 | Ritchie et al. |
| 7,524,320 | B2 | 4/2009 | Tierney et al. |
| 7,722,607 | B2 | 5/2010 | Dumbauld et al. |
| 7,809,184 | B2 | 10/2010 | Neubauer et al. |
| 7,947,051 | B2 | 5/2011 | Lee et al. |
| 7,954,397 | B2 | 6/2011 | Choi et al. |
| 7,963,913 | B2 | 6/2011 | Devengenzo et al. |
| 7,979,157 | B2 | 7/2011 | Anvari |
| 8,021,326 | B2 | 9/2011 | Moll et al. |
| 8,183,520 | B2 | 5/2012 | Prisco |
| 8,392,022 | B2 | 3/2013 | Ortmaier et al. |
| 8,394,054 | B2 | 3/2013 | Wallace et al. |
| 8,479,969 | B2 | 7/2013 | Shelton, IV |
| 8,506,557 | B2 | 8/2013 | Zemlok et al. |
| 8,525,687 | B2 | 9/2013 | Tran |
| 8,828,023 | B2 | 9/2014 | Neff et al. |
| 8,992,113 | B2 | 3/2015 | Campagna et al. |
| 10,751,136 | B2 * | 8/2020 | Farritor ............... A61B 1/051 |
| 2001/0008343 | A1 | 7/2001 | Herdin et al. |
| 2003/0040758 | A1 | 2/2003 | Wang et al. |
| 2004/0054489 | A1 | 3/2004 | Moctezuma De La Barrera et al. |
| 2004/0128026 | A1 | 7/2004 | Harris et al. |
| 2004/0143243 | A1 | 7/2004 | Wahrburg |
| 2004/0254680 | A1 | 12/2004 | Sunaoshi |
| 2005/0113815 | A1 | 5/2005 | Ritchie et al. |
| 2005/0116673 | A1 | 6/2005 | Carl et al. |
| 2006/0264742 | A1 | 11/2006 | Neubauer et al. |
| 2007/0035203 | A1 | 2/2007 | Bromfield |
| 2007/0089557 | A1 | 4/2007 | Solomon et al. |
| 2008/0058861 | A1 | 3/2008 | Cooper et al. |
| 2008/0065105 | A1 | 3/2008 | Larkin et al. |
| 2008/0103491 | A1 | 5/2008 | Omori et al. |
| 2008/0228195 | A1 | 9/2008 | von Jako et al. |
| 2008/0262513 | A1 | 10/2008 | Stahler et al. |
| 2009/0036902 | A1 | 2/2009 | DiMaio et al. |
| 2009/0044655 | A1 | 2/2009 | DeLouis et al. |
| 2009/0163930 | A1 | 6/2009 | Aoude et al. |
| 2009/0171197 | A1 | 7/2009 | Burger et al. |
| 2009/0326324 | A1 | 12/2009 | Munoz Martinez et al. |
| 2010/0082041 | A1 | 4/2010 | Prisco |
| 2010/0286712 | A1 | 11/2010 | Won et al. |
| 2010/0318101 | A1 | 12/2010 | Choi |
| 2010/0332031 | A1 | 12/2010 | Itkowitz et al. |
| 2011/0015650 | A1 | 1/2011 | Choi et al. |
| 2011/0015850 | A1 | 1/2011 | Tange et al. |
| 2011/0022060 | A1 | 1/2011 | Won et al. |
| 2011/0190937 | A1 | 8/2011 | Ortmaier |
| 2011/0224825 | A1 | 9/2011 | Larkin et al. |
| 2011/0290856 | A1 | 12/2011 | Shelton, IV et al. |
| 2012/0029694 | A1 | 2/2012 | Muller |
| 2012/0041263 | A1 | 2/2012 | Sholev |
| 2012/0116416 | A1 | 5/2012 | Neff et al. |
| 2012/0143211 | A1 | 6/2012 | Kishi |
| 2012/0289973 | A1 | 11/2012 | Prisco et al. |
| 2013/0096575 | A1 | 4/2013 | Olson |
| 2013/0123783 | A1 * | 5/2013 | Marczyk ............... A61B 17/29 |
| | | | 606/45 |
| 2013/0131651 | A1 | 5/2013 | Strobl et al. |
| 2013/0144307 | A1 | 6/2013 | Jeong et al. |
| 2013/0193898 | A1 | 8/2013 | Williams et al. |
| 2013/0218024 | A1 | 8/2013 | Boctor et al. |
| 2013/0304086 | A1 | 11/2013 | Tovey et al. |
| 2013/0325033 | A1 | 12/2013 | Schena et al. |
| 2014/0001234 | A1 | 1/2014 | Shelton, IV et al. |
| 2014/0005677 | A1 | 1/2014 | Shelton, IV et al. |
| 2014/0110453 | A1 | 4/2014 | Wingardner et al. |
| 2014/0221738 | A1 * | 8/2014 | Sholev ............... A61B 1/00149 |
| | | | 600/102 |
| 2014/0252071 | A1 | 9/2014 | Moore et al. |
| 2016/0294092 | A1 | 10/2016 | Kikuchi et al. |
| 2016/0338781 | A1 | 11/2016 | Kapadia |
| 2017/0071692 | A1 | 3/2017 | Taylor et al. |
| 2018/0008338 | A1 | 1/2018 | Kopp |

FOREIGN PATENT DOCUMENTS

| | | |
|---|---|---|
| DE | 102014203921 A1 | 9/2015 |
| EP | 2772206 A2 | 9/2014 |
| JP | 2009297326 A | 12/2009 |
| JP | 2016512990 A | 5/2016 |
| JP | 2016513993 A | 5/2016 |
| WO | 9937220 A1 | 7/1999 |
| WO | 2006079108 A1 | 7/2006 |
| WO | 2009151205 A1 | 12/2009 |
| WO | 2010068005 A2 | 6/2010 |
| WO | 2010126127 A1 | 11/2010 |
| WO | 2012112888 A2 | 8/2012 |
| WO | 2013042107 A1 | 3/2013 |
| WO | 2013159933 A1 | 10/2013 |
| WO | 2015175200 A1 | 11/2015 |
| WO | 2016043845 A1 | 3/2016 |
| WO | 2016057778 A1 | 4/2016 |

OTHER PUBLICATIONS

European Search Report dated Aug. 24, 2017, corresponding to European Application No. 14881189.6; 13 pages.
Chinese Office Action (with English translation) dated Jul. 20, 2018, corresponding to Chinese Application No. 201480073374.4; 29 total pages.
European Office Action dated Aug. 7, 2018, corresponding to European Application No. 14 881 189.6; 8 pages.
European Search Report dated Sep. 6, 2018, corresponding to European Application No. 16752762.1; 11 pages.
European Search Report dated Dec. 20, 2017, corresponding to European Application No. 15793145.2; 9 total pages.
European Search Report dated Dec. 7, 2017, corresponding to European Application No. 15792219.6; 11 pages.
Chinese Office Action (with English tranlsation) dated Aug. 21, 2018, corresponding to Chinese Application No. 201580025231.0; 15 total pages.
International Search Report for PCT/US2014/064472 dated Feb. 13, 2015 (5 pages).
International Search Report for PCT/US2016/014002, dated Mar. 21, 2016 (4 pages).
International Search Report for PCT/US2015/027905, dated Jul. 28, 2015 (2 pages).
Chinese Office Action dated Nov. 4, 2020, issued in corresponding Chinese Appln. No. 201780031505, 10 pages.
Australian Office Action dated Mar. 2, 2021, issued in corresponding AU Appln. No. 2017269350, 6 pages.
Japanese Office Action dated Feb. 26, 2021, issued in corresponding Japanese Appln. No. 2018560018, 6 pages.

* cited by examiner

ROBOTIC SURGICAL ASSEMBLIES AND INSTRUMENT DRIVE UNITS THEREOF

CROSS-REFERENCE TO RELATED APPLICATIONS

This application is a U.S. National Stage Application filed under 35 U.S.C. § 371(a) of International Patent Application Serial No. PCT/US2017/034206, filed May 24, 2017, which claims the benefit of and priority to U.S. Provisional patent application Ser. No. 62/341,949, filed May 26, 2016, the entire disclosure of which is incorporated by reference herein.

BACKGROUND

Robotic surgical systems have been used in minimally invasive medical procedures. Some robotic surgical systems included a console supporting a surgical robotic arm and a surgical instrument, having at least one end effector (e.g., forceps or a grasping tool), mounted to the robotic arm. The robotic arm provided mechanical power to the surgical instrument for its operation and movement. Each robotic arm may have included an instrument drive unit operatively connected to the surgical instrument.

Manually-operated surgical instruments often included a handle assembly for actuating the functions of the surgical instrument. However, when using a robotic surgical system, no handle assembly is typically present to actuate the functions of the end effector. Accordingly, to use each unique surgical instrument with a robotic surgical system, an instrument drive unit is used to interface with the selected surgical instrument to drive operations of the surgical instrument.

A need exists for a robotic surgical system having improved and increased usability, a more compact design, and a simplified, less expensive instrument drive unit.

SUMMARY

In accordance with an aspect of the present disclosure, an instrument drive unit for use with a surgical robotic arm is provided. The instrument drive unit includes a body, a first gear, and a driven coupler. The body has a proximal end and a distal end configured to be coupled to a surgical instrument. The first gear is non-rotatably coupled to the proximal end of the body. The driven coupler is disposed at the proximal end of the body and laterally offset from the first gear. The driven coupler is operably coupled to the first gear such that rotation of the driven coupler rotates the first gear to effect rotation of the body about a longitudinal axis defined by the body.

In some embodiments, the instrument drive unit may further include a plate including a first portion and a second portion extending laterally from the first portion. The first portion may have the first gear rotatably disposed therewith. The second portion may have the driven coupler rotatably disposed therewith. The driven coupler may include a first end extending proximally from the plate and a second end extending distally from the plate. The first end may have a toothed outer surface, and the second end may be configured to be non-rotatably coupled to a motor shaft of a surgical instrument holder.

It is contemplated that the instrument drive unit may further include a second gear disposed between the driven coupler and the first gear to transfer rotational motion of the driven coupler to the first gear.

It is envisioned that the instrument drive unit may further include a belt disposed about the driven coupler and the first gear to rotatably interconnect the driven coupler with the first gear. The instrument drive unit may further include an annular member disposed at the proximal end of the body and engaged with an outer surface of the belt to increase a tension of the belt.

In some aspects of the present disclosure, the instrument drive unit may further include an outer housing configured to be non-rotatably connected to the surgical robotic arm. The body is rotatably disposed within the outer housing.

In another aspect of the present disclosure, a surgical assembly for use with a surgical robotic arm is provided. The surgical assembly includes a surgical instrument and an instrument drive unit. The surgical instrument includes a housing, a shaft extending distally from the housing, and an end effector extending distally from the shaft. The instrument drive unit is configured for driving an actuation of the end effector of the surgical instrument. The instrument drive unit includes a body, a first gear, and a drive coupler. The body has a proximal end and a distal end configured to be coupled to the housing of the surgical instrument. The first gear is non-rotatably coupled to the proximal end of the body. The driven coupler is disposed at the proximal end of the body and laterally offset from the first gear. The driven coupler is operably coupled to the first gear such that rotation of the driven coupler rotates the first gear to rotate the body to effect rotation of the surgical instrument about a longitudinal axis defined by the body.

In some embodiments, the surgical assembly may further include a surgical instrument holder. The surgical instrument holder includes a carriage and an outer member extending from the carriage. The carriage has a first side configured for movable engagement to the surgical robotic arm, and a second side having a motor shaft configured for operable engagement with the driven coupler of the instrument drive unit. The outer member may be configured for receipt of the housing of the surgical instrument therein.

It is contemplated that the surgical instrument holder may further include a motor supported in the carriage and drivingly connected to the motor shaft.

It is envisioned that the motor shaft may include a gear for selective connection to a gear of the driven coupler.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein.

DETAILED DESCRIPTION

Figure 1:
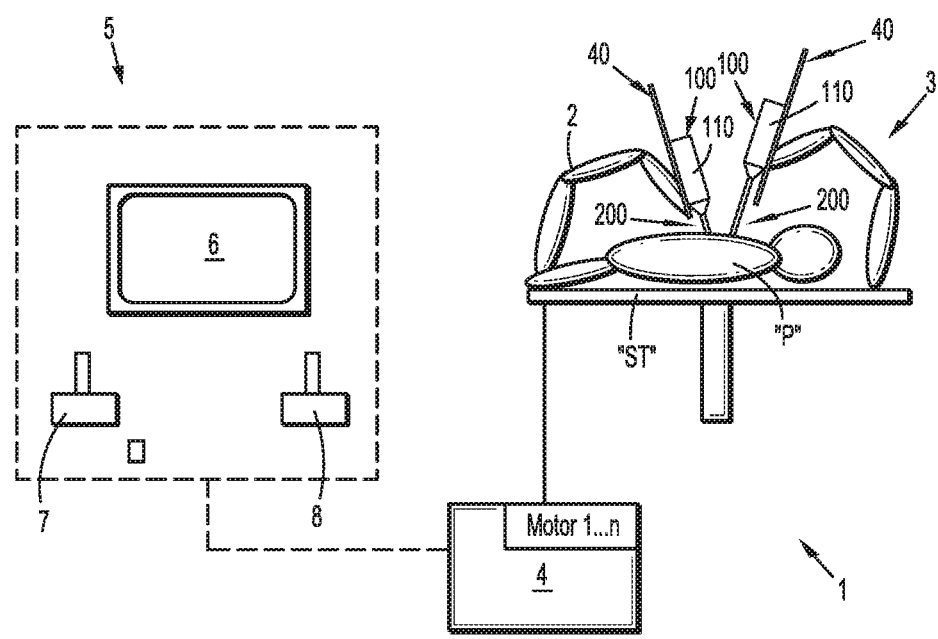
FIG. 1 is a schematic illustration of a robotic surgical system including a robotic surgical assembly in accordance with the present disclosure.

Embodiments of the presently disclosed surgical assembly including an instrument drive unit, a surgical instrument, and a surgical instrument holder, and methods thereof, are described in detail with reference to the drawings, in which like reference numerals designate identical or corresponding elements in each of the several views. As used herein the term "distal" refers to that portion of the surgical instrument holder, surgical instrument, and/or instrument drive unit that is closer to the patient, while the term "proximal" refers to that portion of the surgical instrument holder, surgical instrument, and/or instrument drive unit that is farther from the patient.

Referring initially to FIG. 1, a surgical system, such as, for example, a robotic surgical system 1, generally includes a plurality of surgical robotic arms 2, 3 having a robotic surgical assembly 100 including an electromechanical surgical instrument 200 removably attached to a slide rail 40 of surgical robotic arms 2, 3; a control device 4; and an operating console 5 coupled with control device 4.

Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art. Each of the robotic arms 2, 3 may be composed of a plurality of members, which are connected through joints. Robotic arms 2, 3 may be driven by electric drives (not shown) that are connected to control device 4. Control device 4 (e.g., a computer) may be set up to activate the drives, in particular by means of a computer program, in such a way that robotic arms 2, 3, the attached robotic surgical assembly 100, and thus electromechanical surgical instrument 200 (including an electromechanical end effector 210 (FIG. 2)) execute a desired movement according to a movement defined by means of manual input devices 7, 8. Control device 4 may also be set up in such a way that it regulates the movement of robotic arms 2, 3.

Robotic surgical system 1 is configured for use on a patient "P" lying on a surgical table "ST" to be treated in a minimally invasive manner by means of a surgical instrument, e.g., electromechanical surgical instrument 200. Robotic surgical system 1 may also include more than two robotic arms 2, 3, the additional robotic arms likewise being connected to control device 4 and being telemanipulatable by means of operating console 5. A surgical instrument, for example, electromechanical surgical instrument 200 (including the electromechanical end effector 210), may also be attached to the additional robotic arm.

Control device 4 may control a plurality of motors, e.g., motors (Motor 1 . . . n), with each motor configured to drive movement of robotic arms 2, 3 in a plurality of directions. Further, control device 4 may control a plurality of motors (not shown) of an instrument drive unit 110 of robotic surgical assembly 100 that drive various operations of surgical instrument 200. In addition, control device 4 may control the operation of a rotation motor, such as, for example, a canister motor "M" (FIG. 3) of surgical instrument holder 102, configured to drive a relative rotation of electromechanical surgical instrument 200 about its axis (FIG. 2), as will be described in detail below. In embodiments, each motor of the instrument drive unit 110 can be configured to actuate a drive rod/cable or a lever arm to effect operation and/or movement of electromechanical surgical instrument 200.

For a detailed discussion of the construction and operation of a robotic surgical system, reference may be made to U.S. Pat. No. 8,828,023, entitled "Medical Workstation," the entire contents of which are incorporated by reference herein.

Figure 2:
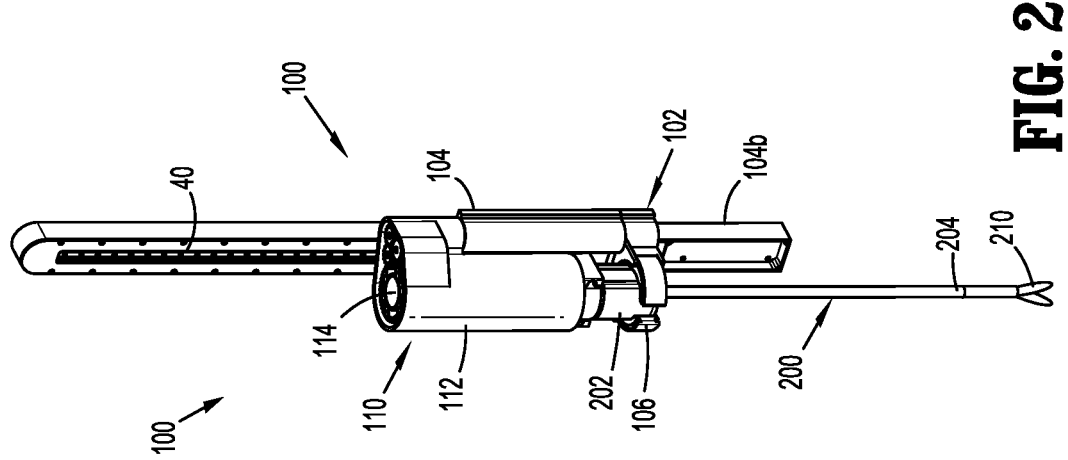
FIG. 2 is a perspective view of the surgical assembly of FIG. 1.

With reference to FIGS. 1 and 2, robotic surgical system 1 includes the robotic surgical assembly 100 that is coupled with or to robotic arm 2 or 3. The robotic surgical assembly 100 includes the surgical instrument holder 102, the instrument drive unit 110, and the electromechanical surgical instrument 200. As partially mentioned above, instrument drive unit 110 transfers power and actuation forces from its motors to driven members of electromechanical surgical instrument 200 to ultimately drive movement of components of end effector 210 of electromechanical surgical instrument 200, for example, a movement of a knife blade (not shown) and/or a closing and opening of jaw members of end effector 210, the actuation or firing of a stapler, and/or the activation or firing of an electrosurgical energy-based instrument, or the like. Instrument drive unit 110 is further configured to rotate electromechanical surgical instrument 200 about longitudinal axis "X" by motor "M" supported in surgical instrument holder 102.

Figure 3:
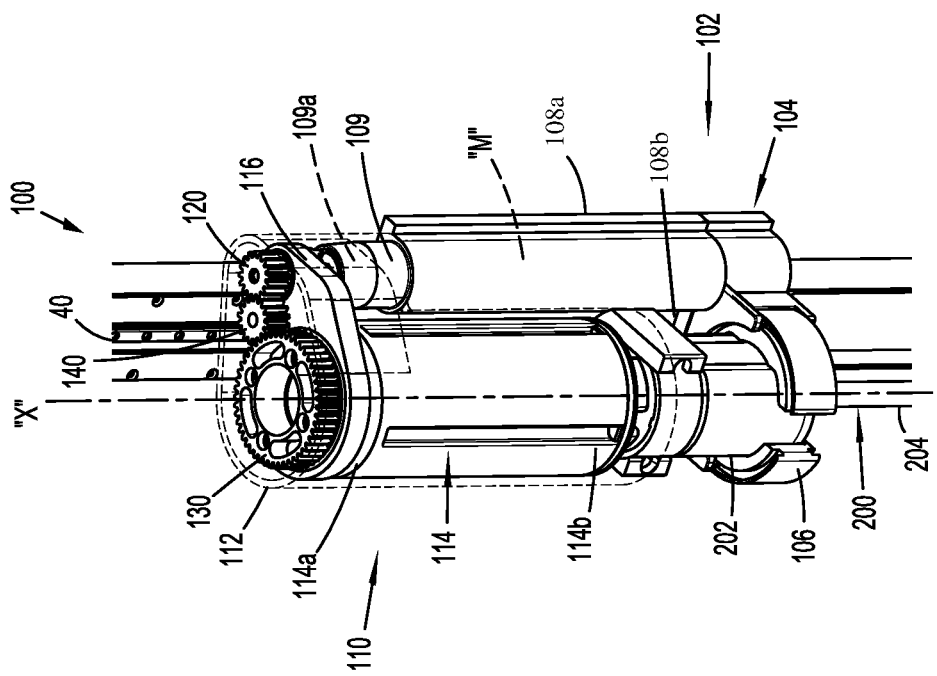
FIG. 3 is an enlarged view, in part phantom, of the surgical assembly of FIG. 2.
Figure 4:
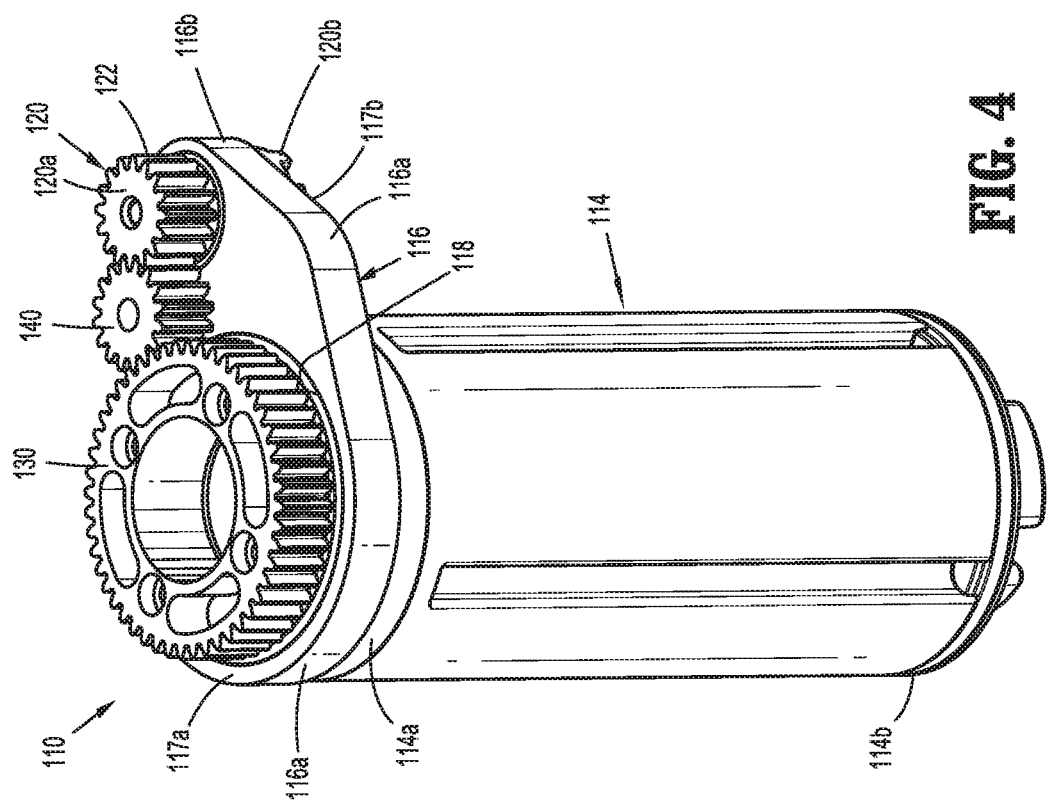
FIG. 4 is a perspective view of an instrument drive unit, with a part removed, of the surgical assembly of FIG. 3.

Turning now to FIGS. 2-4, surgical instrument holder 102 of surgical assembly 100 functions both to actuate a rotation of a body 114 of instrument drive unit 110 and to support a housing 202 of surgical instrument 200. Surgical instrument holder 102 includes a back member or carriage 104, and an outer member 106 extending perpendicularly from an end 104b of carriage 104. In some embodiments, outer member 106 may extend at various angles relative to carriage 104 and from various portions of carriage 104. Carriage 104 has a first side 108a and a second side 108b, opposite first side 108a. First side 108a of carriage 104 is detachably connectable to rail 40 of robotic arm 2. Surgical assembly 100 is configured such that surgical instrument holder 102 may slide or translate along rail 40 of robotic arm 2. Second side 108b of carriage 104 is configured to connect to instrument drive unit 110. In some embodiments, second side 108b of carriage 104 may define a longitudinal track (not shown) configured for slidable receipt of instrument drive unit 110.

Carriage 104 of surgical instrument holder 102 supports or houses a motor, such as, for example, canister motor "M" therein. Motor "M" receives controls and power from control device 4 to selectively rotate an inner housing or body 114 of instrument drive unit 110, as will be described in detail below. Motor "M" has a motor shaft 109 extending longitudinally through carriage 104 that is drivingly connected to gear 120b of instrument drive unit 110. Specifically, motor shaft 109 includes a gear 109a for selective connection to gear 120b of instrument drive unit 110 to effect a rotation of body 114 of instrument drive unit 110 about its longitudinal axis "X."

Outer member 106 of surgical instrument holder 102 is configured to receive and hold housing 202 of surgical instrument 200. Outer member 106 is C-shaped, but in some embodiments, outer member 106 may assume a variety of shapes, such as, for example, U-shaped, V-shaped, hook-shaped, or the like.

With continued reference to FIGS. 2-4, instrument drive unit 110 of surgical assembly 100 includes an outer housing 112 and an inner housing or body 114 rotatably disposed within outer housing 112. Outer housing 112 is coupled to second side 108b of carriage 104 of surgical instrument holder 102 and houses various components of instrument drive unit 110. Body 114 of instrument drive unit 110 has a generally cylindrical configuration and defines a longitudinal axis "X" between proximal and distal ends 114a, 114b thereof. In some embodiments, body 114 may assume a variety of configurations, such as, for example, squared, elongate, tubular, or the like. Distal end 114b of body 114 is configured to be operably connected to driven components of housing 202 of surgical instrument 200 such that actuation of instrument drive unit 110 moves drive shafts disposed within a shaft 204 of surgical instrument 200 to effect actuation of various functions of end effector 210 of surgical instrument 200.

Body 114 of instrument drive unit 110 is configured and dimensioned to slidably receive a motor pack or the like (not shown) therein. The motor pack may include four motors arranged in a rectangular formation such that respective drive shafts (not shown) thereof are all parallel to one another and all extending in a common direction. The drive shaft of each motor may operatively interface with a respective drive coupler (not shown) of a drive transfer assembly (not shown) of instrument drive unit 110. The motor pack may include four canister motors or the like, each having a drive shaft having a non-circular transverse cross-sectional profile (e.g., substantially D-shaped, or the like).

In use, as the motors of the motor pack are actuated, rotation of the drive shafts of the motors is transferred to gears (not shown) of drive assemblies (not shown) of surgical instrument 200 via respective drive transfer shafts (not shown) to actuate various functions of surgical instrument 200.

With reference to FIG. 4, instrument drive unit 110 includes a plate or flange 116 disposed at proximal end 114a of body 114 of instrument drive unit 110 and which is fixed within outer housing 112 of instrument drive unit 110. Plate 116 has a first portion 116a and a second portion 116b extending laterally from first portion 116a. First portion 116a of plate 116 defines an annular cavity 118 through a thickness thereof. Proximal end 114a of body 114 extends through annular cavity 118 of plate 116 and is rotatable therein. Second portion 116b of plate 116 extends radially beyond a periphery of proximal end 114a of body 114 of instrument drive unit 110.

Instrument drive unit 110 further includes a driven coupler 120, a first gear 130, and a second gear 140 disposed between driven coupler 120 and first gear 130 to transfer rotational motion of driven coupler 120 to first gear 130. Each of driven coupler 120, first gear 130, and second gear 140 is rotatably supported on or disposed with plate 116. In particular, driven coupler 120 and second gear 140 are rotatably supported within second portion 116b of plate 116, and first gear 130 is rotatably disposed on first portion 116a of plate 116. As such, driven coupler 120 and second gear 140 are each laterally offset from longitudinal axis "X" of body 114, and first gear 130 is coaxial with longitudinal axis "X" of body 114. Driven coupler 120 has a first end 120a extending proximally from a top surface 117a of plate 116, and a second end 120b extending distally from a bottom surface 117b of plate 116. First end 120a of driven coupler 120 is in the form of a gear (e.g., a spur gear) having a toothed outer surface 122 that is in meshing engagement with second gear 140. Second end 120b of driven coupler 120 is in the form of a gear (e.g., a crown gear) having downward projecting teeth configured to be non-rotatably inter-engaged with gear teeth of gear 109a (FIG. 3) of motor shaft 109 of surgical instrument holder 102.

First gear 130 of instrument drive unit 110 is non-rotatably connected to or fixed with proximal end 114a of body 114 to rotate body 114 therewith. First gear 130 is in meshing engagement with second gear 140 such that rotation of driven coupler 120 rotates first gear 130, via rotation of second gear 140, to effect rotation of body 114 of instrument drive unit 110 about its longitudinal axis "X" relative to outer housing 112 of instrument drive unit 110. In some embodiments, rather than proximal end 114a of body 114 extending proximally through plate 116 to connect to first gear 130, first gear 130 may extend distally from bottom surface 117b of plate 116 to connect to proximal end 114a of body 114.

In operation, prior to or during a surgical procedure, instrument drive unit 110 may be coupled to surgical instrument 200 and surgical instrument holder 102. In particular, a proximal end of housing 202 of surgical instrument 200 is non-rotatably connected to distal end 114b of body 114 of instrument drive unit 110. Instrument drive unit 110, with surgical instrument 200 attached thereto, is positioned relative to surgical instrument holder 102 to operably couple second end or gear 120b of driven coupler 120 of instrument drive unit 110 with gear 109a of motor shaft 109 of surgical instrument holder 102. With instrument drive unit 110 operably coupled to surgical instrument holder 102, motor "M" of surgical instrument holder 102 may be actuated to ultimately effect rotation of surgical instrument 200 within outer member 106 of surgical instrument holder 102.

In particular, actuation of motor "M" of surgical instrument holder 102 drives rotation of motor shaft 109 of surgical instrument holder 102 and gear 109a thereof. Rotation of gear 109a of motor shaft 109 effects rotation of driven coupler 120 of instrument drive unit 110, which has its second end 120b in meshing engagement with gear 109a of motor shaft 109. Rotation of driven coupler 120 rotates second gear 140, which is in meshing engagement with toothed outer surface 122 of first end 120a of driven coupler 120. Rotation of second gear 140 results in rotation of first gear 130 due to first and second gears 130, 140 being in meshing engagement with one another. Rotation of first gear 130 effects rotation of body 114 of instrument drive unit 110 about its longitudinal axis "X" since first gear 130 is non-rotatably connected to proximal end 114a of body 114 of instrument drive unit 110. With housing 112 of surgical instrument 200 non-rotatably coupled to distal end 114b of body 114 of instrument drive unit 110, rotation of body 114 of instrument drive unit 110 results in rotation of surgical instrument 200 about longitudinal axis "X."

Figure 5:
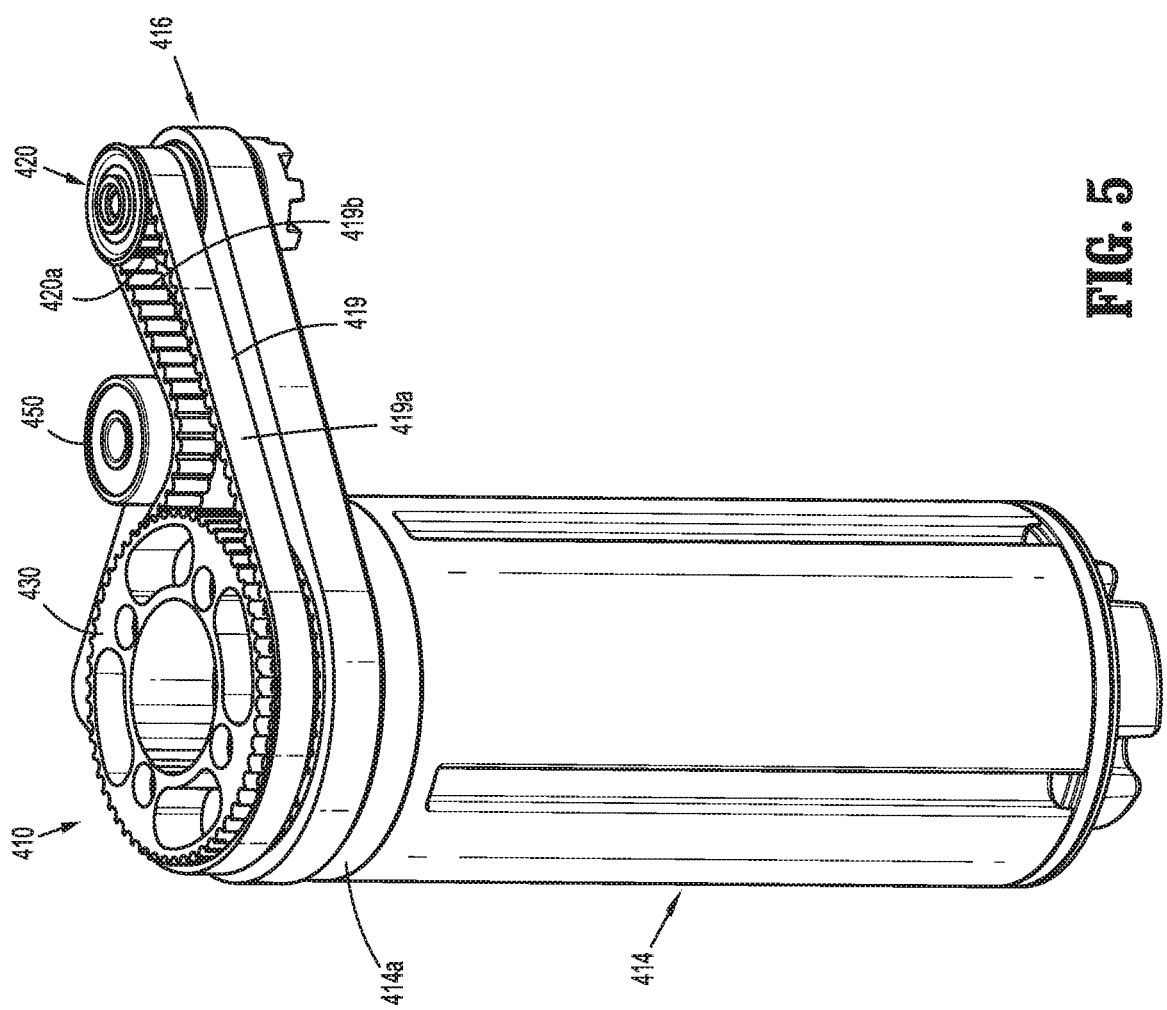
FIG. 5 is a perspective view of another embodiment of an instrument drive unit, with a part removed, for use with the robotic surgical system of FIG. 1.

As shown in FIG. 5, another embodiment of an instrument drive unit is provided by the present disclosure, and is generally designated using reference numeral 410. Instrument drive unit 410 is similar to instrument drive unit 110 described above with respect to FIGS. 2-4, and therefore will only be described to the extent necessary to highlight the differences between instrument drive units 110, 410.

Instrument drive unit 410 includes an outer housing (not shown), a body 414, a plate 416, a first gear 430, and a driven coupler 420, each being similar to the corresponding components of instrument drive unit 110 described above. Rather than having a gear-to-gear connection between driven coupler 420 and first gear 430, as is the case with instrument drive unit 110, body 414 of instrument drive unit 410 includes a belt or strap 419 disposed about driven coupler 420 and first gear 430 to rotatably interconnect driven coupler 420 with first gear 430. Belt 419 has an outer surface 419a, and an inner surface 419b defining a plurality of gear teeth. The gear teeth of belt 419 are in meshing engagement with a toothed outer surface 420a of driven coupler 420 and teeth of first gear 430 such that rotation of driven coupler 420 rotates belt 419, which results in rotation of first gear 430 to effect rotation of body 414 about its longitudinal axis.

Instrument drive unit 410 further includes an annular member or idler 450 disposed at a proximal end 414a of body 414 and is engaged with outer surface 419a of belt 419 to increase a tension of belt 419. Placement of annular member 450 may be selectively adjusted to adjust the tension of belt 419, and thus alter the resistance to rotation of driven coupler 420 and first gear 430, and facilitate assembly, repair, and adjustments.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An instrument drive unit for use with a surgical robotic arm, comprising:
   a body having a proximal end and a distal end configured to be coupled to a surgical instrument, the body defining a longitudinal axis;
   a first gear non-rotatably coupled to the proximal end of the body;
   a driven coupler disposed at the proximal end of the body and laterally offset from the first gear, wherein the driven coupler is operably coupled to the first gear such that rotation of the driven coupler rotates the first gear to effect rotation of the body about the longitudinal axis; and
   a plate including:
      a first portion having the first gear rotatably disposed therewith; and
      a second portion extending laterally from the first portion and having the driven coupler rotatably disposed therewith,
   wherein the driven coupler includes:
      a first end extending proximally from the plate and having a toothed outer surface; and
      a second end extending distally from the plate and configured to be non-rotatably coupled to a motor shaft of a surgical instrument holder.

2. The instrument drive unit according to claim 1, further comprising a second gear disposed between the driven coupler and the first gear to transfer rotational motion of the driven coupler to the first gear.

3. The instrument drive unit according to claim 1, further comprising a belt disposed about the driven coupler and the first gear to rotatably interconnect the driven coupler with the first gear.

4. The instrument drive unit according to claim 3, further comprising an annular member disposed at the proximal end of the body and engaged with an outer surface of the belt to increase a tension of the belt.

5. The instrument drive unit according to claim 1, further comprising an outer housing configured to be non-rotatably connected to the surgical robotic arm, the body being rotatably disposed within the outer housing.

6. A surgical assembly for use with a surgical robotic arm, comprising:
   a surgical instrument including:
      a housing;
      a shaft extending distally from the housing; and
      an end effector extending distally from the shaft;
   an instrument drive unit configured for driving an actuation of the end effector of the surgical instrument, the instrument drive unit including:
      a body having a proximal end and a distal end configured to be coupled to the housing of the surgical instrument, the body defining a longitudinal axis;
      a first gear non-rotatably coupled to the proximal end of the body; and
      a driven coupler disposed at the proximal end of the body and laterally offset from the first gear, wherein the driven coupler is operably coupled to the first gear such that rotation of the driven coupler rotates the first gear to rotate the body to effect rotation of the surgical instrument about the longitudinal axis; and
   a surgical instrument holder including:
      a carriage having a first side configured for movable engagement to the surgical robotic arm, and a second side having a motor shaft configured for operable engagement with the driven coupler of the instrument drive unit; and
      an outer member extending from the carriage and configured for receipt of the housing of the surgical instrument therein.

7. The surgical assembly according to claim 6, wherein the instrument drive unit further includes a plate including:
   a first portion having the first gear rotatably disposed therewith; and
   a second portion extending laterally from the first portion and having the driven coupler rotatably disposed therewith.

8. The surgical assembly according to claim 7, wherein the driven coupler includes:
   a first end extending proximally from the plate and having a toothed outer surface; and
   a second end extending distally from the plate and configured to be non-rotatably coupled to the motor shaft of the surgical instrument holder.

9. The surgical assembly according to claim 6, wherein the instrument drive unit further includes a second gear disposed between the driven coupler and the first gear to transfer rotational motion of the driven coupler to the first gear.

10. The surgical assembly according to claim 6, wherein the instrument drive unit further includes a belt disposed about the driven coupler and the first gear to rotatably interconnect the driven coupler with the first gear.

11. The surgical assembly according to claim 10, wherein the instrument drive unit further includes an annular member disposed at the proximal end of the body and engaged with an outer surface of the belt to increase a tension of the belt.

12. The surgical assembly according to claim 6, wherein the instrument drive unit further includes an outer housing configured to be non-rotatably connected to the surgical robotic arm, the body of the instrument drive unit being rotatably disposed within the outer housing.

13. The surgical assembly according to claim 6, wherein the surgical instrument holder further includes a motor supported in the carriage and drivingly connected to the motor shaft.

14. The surgical assembly according to claim 13, wherein the motor shaft includes a gear for selective connection to a gear of the driven coupler.

* * * * *